United States Patent [19]

Inoue et al.

[11] Patent Number: 5,350,680

[45] Date of Patent: Sep. 27, 1994

[54] CEPHALOSPORINASE TESTING AGENT

[75] Inventors: Matsuhisa Inoue, Seta; Akira Sakai, Tokyo, both of Japan

[73] Assignee: Showa Yakuhin Kako Co., Ltd., Tokyo, Japan

[21] Appl. No.: 976,993

[22] PCT Filed: Dec. 18, 1991

[86] PCT No.: PCT/JP91/01732

§ 371 Date: Feb. 2, 1993

§ 102(e) Date: Feb. 2, 1993

[87] PCT Pub. No.: WO92/11386

PCT Pub. Date: Jul. 9, 1992

[30] Foreign Application Priority Data

Dec. 21, 1990 [JP] Japan ................................ 2-405144

[51] Int. Cl.$^5$ ...................... C12Q 1/04; A61K 31/43
[52] U.S. Cl. .......................................... 435/34; 435/18; 435/32; 435/49; 435/231; 435/810; 435/975; 514/192; 514/200
[58] Field of Search ...................... 435/34, 18, 32, 49, 435/231, 810, 975; 514/192, 200

[56] References Cited

U.S. PATENT DOCUMENTS 5,026,638  6/1991  Saperstein ............................. 435/32

FOREIGN PATENT DOCUMENTS 0322591  7/1989  European Pat. Off. ........ C12Q 1/04
1594001  7/1981  United Kingdom ........... C12Q 1/00
2128737  5/1984  United Kingdom ........... C12Q 1/04

OTHER PUBLICATIONS

Chemical Abstracts, vol. 93, No. 7; Azuma et al.; Inhibitors of Beta-Lactamase; p. 174.
Journal of Immunological Methods; vol. 83, 1985; pp. 371–377; Premier et al.; "An Evaluation of . . . Immunoassay".
Antimicrob Agents Chemother, vol. 33, No. 3 (1989), K. Bush "Classification of β-Iactamases: Groups 1, 2a, 2b, and 2b'" p. 264–270.
Chemotherapy, vol. 36, No. 3, (1990), W. Cullmann "Interaction of β-Lactamase Inhibitors with Various –Lactamase Inhibitors with Various β-Lactamases" pp. 200–208.
Kobayashi et al., *Antimicrobial Agents and Chemotherapy*, vol. 32, No. 7, pp. 1040–1045, 1988.
Labia et al., *Chemical Abstracts*, vol. 92, p. 199, Ref. #89743q, 1980 (Ann. Microbiol. (Paris), 1979, 130B(3), 295–304).
Cullman, *Chemotherapy*, vol. 36, No. 3, pp. 200–208, 1990.
Toda et al., *The Journal of Antibiotics*, vol. 34, No. 11, pp. 1469–1475, Nov. 1981.
Sato et al., *Antimicrobial Agents and Chemotherapy*, vol. 22, No. 4, pp. 579–584, Oct. 1982.
Nkazawa et al., *Chemical Abstracts*, vol. 106, p. 335, Ref. #116381m, 1987 (Chemotherapy (Tokyo) 1986, 34 (Suppl. 4) 1–8).
Stahl et al., *Chemical Abstracts*, vol. 96, p. 266, Ref. #81892z, 1982 (Ger. Offen. DE 3,019,451).
Blechschmidt et al., *Chemical Abstracts*, vol. 117, p. 395, Ref. #43279z, 1992 (J. Gen. Microbiol. 1992, 38(6), 1197–202).
Cordin et al., *Chemical Abstracts*, vol. 114, p. 451, Ref. #203396d, 1991 (J. Int. Med. Res. 1990, 18 (Suppl. 4) 670–770).
Kitzis et al., *Chemical Abstracts*, vol. 111, p. 424, Ref. #228866h, 1989 (Eur. J. Clin. Microbiol. Infect. Dis. 1989, 8(9) 783–788).

*Primary Examiner*—Michael G. Wityshyn
*Assistant Examiner*—Abdel A. Mohamed
*Attorney, Agent, or Firm*—Cushman, Darby & Cushman

[57] ABSTRACT

A cephalosporinase testing agent comprising a cephalosporin antibiotic, a penicillinase inhibitor in an amount of 20% by weight or less based on the weight of the cephalosporin-antibiotic, and a pH indicator which may be bromcresol purple is provided. A cephalosporinase producing bacteria can be judged by smearing a sample containing bacteria to be tested on the testing agent and observing the color tone change. According to this agent, cephalosporinase-active penicillinase producing bacteria are judged cephalosporinase-negative owing to the action of the penicillinase inhibitor, which may be clavulanic acid. Therefore, since only cephalosporinase producing bacteria are judged cephalosporinase-positive, this agent enables error free judgment.

8 Claims, No Drawings

CEPHALOSPORINASE TESTING AGENT

TECHNICAL FIELD

The present invention relates to a cephalosporinase testing agent.

More specifically, the present invention relates to a cephalosporinase testing agent which enables a correct judgment as to whether or not infection-causing bacteria separated from a patient of a bacterial infectious disease are cephalosporinase-producing bacteria or not.

BACKGROUND ART

Beta-lactam antibiotics are nowadays frequently used for chemotherapy of infectious diseases. However, cephalosporin antibiotics and penicillin antibiotics, both beta-lactam antibiotics, are degraded by cephalosporinases and penicillinases, respectively, and consequently loose their antibacterial activity. For this reason, treatment by beta-lactam antibiotics can not be expected to have the desired effect as the infection-causing bacteria in a patient are beta-lactamase producing bacteria. In choosing a drug for the treatment of an infectious disease, it is thus important to judge beforehand whether or not infection-causing bacteria are beta-lactamase producing bacteria.

The detection of a beta-lactamase has been so far carried out by combined detection using a penicillinase testing agent comprising a penicillin antibiotic as a substrate together with a pH indicator as well as a cephalosporinase testing agent comprising a cephalosporin antibiotic and a pH indicator. In these testing agents, the substrate for an enzyme, i.e., a penicillin antibiotic and a cephalosporin antibiotic, is hydrolyzed to afford an acid where the bacteria tested are penicillinase producing bacteria and cephalosporinase producing bacteria, respectively, and as a result, a pH indicator contained in the testing agent will change its color. Consequently, the bacteria tested are judged to be bacteria which produce both penicillinase and cephalosporinase, where they are found as positive by each testing agent.

In general, penicillinases specifically hydrolyze penicillin antibiotics, and cephalosporinases specifically hydrolyze cephalosporin antibiotics. However, some penicillinases are known to hydrolyze not only penicillin antibiotics but also cephalosporin antibiotics as substrates. If such cephalosporinase-active penicillinase producing bacteria are subjected to the judgment according to the method described above, they will be found positive by each testing agent. As a result, bacteria producing a beta-lactamase actually classified as a penicillinase will be misjudged as bacteria producing both penicillinase and cephalosporinase. Such misjudgments sometimes lead to an improper choice of the chemotherapeutic in clinical treatment.

Accordingly, an object of the present invention is to provide a beta-lactamase testing agent which enables a proper and easy judgment of the type of beta-lactamase with no possibility of a misjudgment. In particular, its object is to provide a cephalosporinase testing agent which avoids a misjudgment on a cephalosporinase-active penicillinase that degenerates cephalosporin antibiotics. The inventors of the present invention have conducted various research, and as a result, they found that the above objects can be attained by providing a cephalosporinase testing agent which is added with a penicillinase inhibitor in addition to a cephalosporin antibiotic as a substrate for the enzyme for the detection of a cephalosporinase.

DISCLOSURE OF INVENTION

According to the present invention, there is provided a cephalosporinase testing agent comprising a cephalosporin antibiotic, a penicillinase inhibitor in an amount of 20% by weight or less based on the weight of the cephalosporin antibiotic, and a pH indicator.

The penicillinase inhibitor contained in the cephalosporinase testing agent of the present invention inhibits the activity of a penicillinase which hydrolyzes a cephalosporin antibiotic. As a consequence, bacteria producing cephalosporinase-active penicillinases are judged as cephalosporinase-negative by the cephalosporinase testing agent of the present invention. On the other hand, since a cephalosporinase can hydrolyze a cephalosporin antibiotic as a substrate without being affected by a penicillinase inhibitor, bacteria producing a cephalosporinase are judged as cephalosporinase-positive.

In addition, the present invention provides a cephalosporinase testing agent further comprising a pH adjusting agent, and a cephalosporinase testing agent supported on a substrate.

Further, the present invention also provides a kit for detecting a cephalosporinase which comprises the above-described cephalosporinase testing agent and a reference testing agent comprising a penicillinase inhibitor and a pH indicator.

BEST MODE FOR CARRYING OUT THE INVENTION

As the cephalosporin antibiotics contained in the cephalosporinase testing agent of the present invention, any cephalosporin antibiotics may be used insofar as they are hydrolyzed by a cephalosporinase to give an acid. Examples of the cephalosporin antibiotics include, for example, cefalexin, cefaclor, cefaloglycin, cefadroxil, cefatrizine, cefamandole, cefradine, cefroxadine, cefapirin, cefalotin, cefaloridine, cefotiam, ceftezole, cefazolin, and cefacetoril, which are known and readily available cephalosporin antibiotics. One or more of these cephalosporin antibiotics may be used.

As the penicillinase inhibitor contained in the cephalosporinase testing agent of the present invention, those specifically affecting penicillinases and inhibiting the activity of penicillinases may be used. An example of such penicillinase inhibitors is clavulanic acid.

The penicillinase inhibitor is contained in the cephalosporinase testing agent in an amount that does not adversely affect the activity of cephalosporinases and that effectively inhibits the activity of penicillinases. The amount of the penicillinase inhibitor varies depending on the kind of the cephalosporin antibiotics used, the type of the penicillinase inhibitor, and the type of beta-lactamase to be tested, and preferably, is appropriately increased or decreased in light of these factors. In general, the amount of penicillinase inhibitor is 20% by weight or less, preferably 0.5 to 5.0% by weight, based on the weight of the cephalosporin antibiotic used.

The pH indicator contained in the cephalosporinase testing agent of the present invention indicates a lowering of pH by a color tone change which is attributed to an acid that is produced from the cephalosporin antibiotic subjected to a hydrolyzation by the action of a cephalosporinase. Any pH indicator may be used insofar as it can meet the above-described purpose. An example of a pH indicator that can detect the change in from an alkaline condition of about pH 8.8 or more to a weak alkaline condition of about pH 7.2 or more is cresol red. An example of a pH indicator that can detect the change from a neutral condition to a weak acidic condition of about pH 5.2 or less is bromphenol red. A pH indicator that has a transition interval between the range of from pH 5 to pH 9 may preferably used. Examples of such pH indicators include bromcresol purple, bromthymol blue, and neutral red. These pH indicators are generally used in an amount of 2% by weight or less based on the weight of the cephalorporin antibiotic.

The cephalosporinase testing agent of the present invention may contain a pH adjusting agent. Examples of the pH adjusting agent include water-soluble basic compounds such as sodium hydroxide and potassium hydroxide. The pH of the cephalosporinase testing agent is preferably adjusted to a pH of not less than the transition interval of the pH indicator used. The pH adjusting agent may be added, for example, in an amount of 2% by weight or less based on the weight of the cephalosporin antibiotic.

The cephalosporinase testing agent of the present invention is generally prepared as a composition in the form of a solid or liquid. For example, where the preparation of the cephalosporinase testing agent in the form of a solid is carried out, it can be manufactured by uniformly mixing the above-described ingredients in the form of powders using a ball mill, a jet mill, or the like. The formulation process is preferebly carried out under a condition of, for example, at a relative humidity of 50% or less and at room temperature or a temperature lower than room temperature. Where the cephalosporinase testing agent in the form of a liquid is prepared, the above-described ingredients may be dissolved in, for example, distilled water for injection, sterilized saline, sterilized purified water, or alcohols. For example, the cephalosporinase testing agent in the form of a liquid may be prepared so that the concentration of the cephalosporin antibiotic is between the range of from 5 to 10% by weight. For the preparation of the cephalosporinase testing agent in the form of a solid, the cephalosporinase testing agent in the form of a liquid prepared in the manner described above can be lyophilized.

Additives such as polyvinyl pyrrolidone may optionally be added for the preparation of the cephalosporinase testing agent of the present invention. These additives are generally used at a concentration of 1% by weight or less. The cephalosporinase testing agent of the present invention may further contain a medium composition for cultivation and the like. Examples of the medium composition for cultivation include agar-containing mediums such as Mueller Hinton agar, heart infusion agar, and brain infusion agar. Where these medium compositions are used, the cephalosporinase testing agent of the present invention may be in the form of a semi-solid.

Preferred embodiments of the cephalosporinase testing agent of the present invention include a cephalosporinase-testing agent that is supported on a substrate. Examples of the substrate include cellulose filters such as paper filter; synthetic resin filter such as polyvinyl alcohol sponge; glass filters made of porous glass; absorbents made of water retensible polymer such as urethane foam; micro-wells such as a micro plate; porous ceramics such as a porous plate; and capillaries utilizing capillary attraction. Cellulose filters are preferably used as the substrate.

Examples of the method for preparing these cephalosporinase testing agents supported on substrates include, for example, a process comprising the steps of impregnating the above-described composition in the form of a solution into a substrate such as a cellulose filter, and drying the resulting filter, if necessary, or a process comprising the step of absorbing a composition in the form of a solution into a capillary glass or the like, and tightly sealing it, if necessary. The drying of the filter that is impregnated with the composition in the form of a solution may be carried out at 60 ° C. for 1 hour. This drying process is preferably conducted to obtain a filter having a water content of 5% or less. In addition, an example of a process for fixing a composition in the form of a solid to a substrate includes the process described in Japanese Patent Publication No.2066/1983.

Examples of the method for using the cephalosporinase testing agent of the present invention include a process comprising the steps of picking up a colony of bacteria to be tested from a cultured medium, and then rubbing the bacteria on the cephalosporinase testing agent of the present invention; or a process of dripping a concentrated bacterial medium on the cephalosporinase testing agent of the present invention. The above-described processes for using the cephalosporinase testing agent typically comprise the steps of rubbing a sample on the testing agent; letting the testing agent stand as it is for about 20 to 30 minutes at room temperature, preferably at 25 ° C.; and observing the color tone change of the testing agent. Where a dried cephalosporinase testing agent fixed onto a substrate is used, the process may further comprise a step of impregnating an appropriate amount of sterilized water, sterilized saline, or the like into the testing agent before its use.

As a preferred embodiment of the present invention, there can be used a cephalosporinase testing agent which comprises bromthymol blue and is adjusted to approximately pH 8 with a pH adjusting agent before being used. According to this embodiment of the testing agent, a judgment cephalosporinase-positive is made when the color tone changes from blue-purple to yellow. In addition, if the testing agent of the present invention is used in combination with a commercially available penicillinase testing agent, the type of the beta-lactamase can accurately determined according to the criteria set out below. Furthermore, the present invention provides a cephalosporinase testing kit which comprises a combination of a reference testing agent containing no antibiotic with the above-described cephalosporinase testing agent. By using this kit, more accurate judgment on cephalosporinases can be achieved. The judgment criteria are shown in Table 1 set out below where the cephalosporinase testing agent and the kit of the present invention are used.

TABLE 1

| | |
|---|---|
| Positive solely to a penicillinase testing agent | Penicillinase producing bacteria |
| Positive solely to the present cephalosporinase testing agent | Cephalosporinase producing bacteria |
| Positive to both a penicillinase testing agent and the present cephalosporinase testing agent | Bacteria producing both penicillinase and cephalosporinase |
| Positive to a reference testing agent | cannot be judged |

The present invention will be hereinafter explained more specifically by way of examples. However, the present invention is not limited to these examples.

EXAMPLE 1

(1) Penicillinase testing agent A

Benzylpenicillin potassium (7.5 g) as substrate of penicillinase, 50 mg of bromcresol purple as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

(2) Cephalosporinase testing agent A of the present invention

Cefaloridine (7.5 g) as substrate of cephalosporinase, 50 mg of clavulanic acid as an inhibitor of penicillinase, 10 mg of bromcresol purple as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

(3) Reference testing agent A

Bromcresol purple (50 mg) as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

EXAMPLE 2

(1) Penicillinase testing agent B

Ampicillin sodium (7.5 g) as substrate of penicillinase, 50 mg of bromthymol blue as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

(2) Cephalosporinase testing agent B of the present invention

Cefazolin (7.5 g) as substrate of cephalosporinase, 50 mg of clavulanic acid as an inhibitor of penicillinase, 50 mg of bromthymol blue as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

(3) Reference testing agent B

Bromthymol blue (50 mg) as a pH indicator, and 25 mg of sodium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

EXAMPLE 3

(1) Penicillinase testing agent C

Phenethicillin (7.5 g) as substrate of penicillinase, 50 mg of neutral red as a pH indicator, and 25 mg of potassium hydroxide as a pH adjusting agent were dissolved in sterilized purified water (100 ml). An 8 mm paper disc punched from Toyo's filter paper No. 526 was impregnated with 0.02 ml of this solution, and then dried by an ordinary method.

(2) Cephalosporinase testing agent C of the present invention

Cefalotin sodium (7.5 g) as substrate of cephalosporinase, 50 mg of clavulanic acid as an inhibitor of penicillinase, 50 mg of neutral red as a pH indicator, and 25 mg of potassium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

(3) Reference testing agent C

Neutral red (50 mg) as a pH indicator, and 25 mg of potassium hydroxide as a pH adjusting agent were dissloved in sterilized purified water (100 ml). An 8 mm paper disc punched from Toyo's filter paper No. 526 was impregnated with 0.02 ml of this solution, and then dried by an ordinary method.

Preparation of beta-lactamase enzymatic solution

Beta-lactamase enzymatic solution was prepared in the manner described below using beta-lactamase whose enzymatic type and activity were known.

(1) Penicillinase extracted and purified from *B. cereus* (Penicillinase A)

Commercially available penicillinase (SIGMA: PCase Type I) was used to prepared an 1 U/ml solution. This penicillinase, one of the most typical, is almost totally unable to hydrolyze cephalosporin antibiotics.

(2) Cephalosporinase extracted and purified from *E. cloacae* (Cephalosporinase A)

Commercially available penicillinase (SIGMA: CSase Type IV) was used to prepare an 1 U/ml solution. This cephalospollinase, one of the most typical, is slightly active in hydrolyzing penicillin antibiotics.

(3) Cephalosporinase-active penicillinase derived from *E. cloacae* (Penicillinase B)

Extraction from *E. cloacae* was carried out according to the method of Inoue (Method for testing beta-lactamase-measurement of enzymatic activity and method for determining its-substrate specificity, Kensa to Gijutsu, 16(3):239-243, 1988), and an 1 U/ml solution was prepared. Although this penicillinase was classified as penicillinase from its enzymatic type, it exhibited potent activity of hydrolyzation to both penicillin antibiotics and cephalosporin antibiotics.

Judgment of beta-lactamase

Each beta-lactamase described above (5 μl) was applied and coated on Penicillinase testing agent A, cephalosporinase testing agent A, and Reference testing agent A described in Exmple 1, and after 30 minutes' standing at room temperature, judgment was carried out according to the judgment criteria in Table 1. The results obtained are shown in Table 2 below. The results of comparative examples are shown in Table 3 in which judgment was conducted in a similar manner using commercially available beta-lactamase detecting discs PCG and CER (Cerotec) as beta-lactamase testing agents.

TABLE 2

| Testing agent | Penicillinase A | Cephalosporinase A | Penicillinase B |
|---|---|---|---|
| Penicillinase testing agent A | + | − | + |
| Cephalosporinase testing agent A | − | + | − |
| Reference testing agent A | − | − | − |
| Enzymatic type determined | Penicillinase | Cephalosporinase | Penicillinase |

TABLE 3

| Testing agent | Penicillinase A | Cephalosporinase A | Penicillinase B |
|---|---|---|---|
| PCG disc | + | − | + |
| CER disc | − | + | + |
| Reference testing agent A | − | − | − |
| Enzymatic type determined | Penicillinase | Cephalosporinase | Cephalosporinase & Penicillinase |

EXAMPLE 4

(1) Penicillinase testing agent D

Benzylpenicillin potassium (7.5 g) as substrate of penicillinase, 60 mg of bromcresol purple as a pH indicator, and 40 mg of sodium hydroxide as a pH adjusting agent were evenly dispersed in isopropanol (100 ml). An 8 mm paper disc punched from Toyo's filter paper No. 526 was impregnated with 0.02 ml of this dispersion, and then dried by an ordinary method.

(2) Cephalosporinase testing agent D of the present invention

Cefaloridine (7.5 g) as substrate of cephalosporinase, 250 mg of clavulanic acid as an inhibitor of penicillinase, 60 mg of bromcresol purple as a pH indicator, and 120 mg of sodium hydroxide as a pH adjusting agent were evenly dispersed in isopropanol (100 ml). An 8 mm paper disc punched from Toyo's filter paper No. 526 was impregnated with 0.02 ml of this dispersion, and then dried by an ordinary method.

(3) Reference testing agent D

Bromcresol purple (60 mg) as a pH indicator, and 40 mg of sodium hydroxide as a pH adjusting agent were evenly dispersed in isopropanol (100 ml). An 8 mm paper disc punched from Toyo's filter paper No. 526 was impregnated with 0.02 ml of this dispersion, and then dried by an ordinary method.

(4) Reference testing agent E

Cefaloridine (7.5 g) as substrate of cephalosporinase, 60 mg of bromcresol purple as a pH indicator, and 120 mg of sodium hydroxide as a pH adjusting agent were evenly dispersed in isopropanol (100 ml). An 8 mm paper disc punched from Toyo's filter paper No. 526 was impregnated with 0.02 ml of this dispersion, and then dried by an ordinary method.

Judgment of beta-lactamase

The above-described testing agents were used to determine the types of beta-lactamase derived from 287 bacterial strains including ATCC standard strains (10 bacteiral species, 25 strains) and clinically isolated strains (25 bacterial species, 262 strains). The results are shown in Table 4. Reference testing agent E exhibited a higher cephalosporinase positive rate than cephalosporinase testing agent D of the present invention. However, the positive rate of 43.9% includes misjudgments in which several cephalosporinase-active penicillinases were judged as cephalosporinase-positive.

TABLE 4

| Testing Agent | Positive Rate (%) |
|---|---|
| Penicillinase testing agent D | 31.4 |
| Cephalosporinase testing agent D | 31.7 |
| Reference testing agent D | 0 |
| Reference testing agent E | 43.9 |

Industrial Applicability

From the foregoing description, it will be understood that the cephalosporinase testing agent of the present invention can accurately judge beta-lactamase types. It is useful for accurate and rapid judgment of the type of beta-lactamase, particularly since it judges as cephalosporinase-negative tested bacteria that produce cephalosporinase-active penicillinase which hydrolyzes cephalosporin antibiotics as its substrate.

We claim:

1. A cephalosporinase testing agent comprising a cephalosporin antibiotic selected from the group consisting of cefalexin, cefaclor, cefaloglycin, cefadroxil, cefatrizine, cefamandole, cefradine, cefroxadine, cefapirin, cefalotin, cefaloridine, cefotiam, ceftezole, cefazolin and cefacetoril, a penicillinase inhibitor in an amount of 0.5 to 5% by weight based on the weight of the cephalosporin antibiotic, and a pH indicator.

2. The cephalosporinase testing agent according to claim 1 further comprising a pH adjusting agent.

3. The cephalosporinase testing agent according to claim 1 supported on a substrate by impregnating the substrate with the testing agent in the form of solution.

4. The cephalosporinase testing agent according to claim 1, wherein the penicillinase inhibitor is clavulanic acid.

5. The cephalosporinase testing agent according to claim 1, wherein the pH indicator has a transition interval in the range of from pH 5 to pH 9.

6. The cephalosporinase testing agent according to claim 1, wherein the penicillinaset inhibitor is clavulanic acid and the pH indicator is bromcresol purple.

7. A kit for detecting a cephalosporinase comprising a reference testing agent including a penicillinase inhibitor and a pH indicator and the beta-lactamase testing agent according to any one of claims 1 to 6.

8. A method for testing a sample from the presence of a cephalosporinase which comprises the steps of (a) smearing a sample comprising bacteria to be tested on a cephalosporinase testing agent comprising a cephalosporin antibiotic selected from the group consisting of cefalexin, cefaclor, cefaloglycin, cefadroxil, cefatrizine, cefamandole, cefradine, cefroxadine, cefapirin, cefalotin, cefaloridine, cefotiam, ceftezole, cefazolin and cefacetoril, a penicillinase inhibitor in an amount of 0.5 to 5% by weight based on the weight of the cephalosporin antibiotic, and a pH indicator, and (b) observing any change of color of the testing agent.

* * * * *